(12) United States Patent
Crawford et al.

(10) Patent No.: US 9,637,440 B2
(45) Date of Patent: May 2, 2017

(54) DERIVATIZATION OF CARBON

(71) Applicant: SCHLUMBERGER TECHNOLOGY CORPORATION, Sugar Land, TX (US)

(72) Inventors: Lynne Crawford, Harlow (GB); Nathan Lawrence, Wyton (GB); Timothy Jones, Cottenham (GB)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 361 days.

(21) Appl. No.: 14/365,945

(22) PCT Filed: Dec. 21, 2012

(86) PCT No.: PCT/IB2012/057619
§ 371 (c)(1),
(2) Date: Jun. 16, 2014

(87) PCT Pub. No.: WO2013/093884
PCT Pub. Date: Jun. 27, 2013

(65) Prior Publication Data
US 2014/0332413 A1    Nov. 13, 2014

(30) Foreign Application Priority Data
Dec. 21, 2011 (GB) .................... 1122050.6

(51) Int. Cl.
*C07C 201/12* (2006.01)
*C01B 31/04* (2006.01)
(Continued)

(52) U.S. Cl.
CPC ............ *C07C 201/12* (2013.01); *B82Y 30/00* (2013.01); *B82Y 40/00* (2013.01);
(Continued)

(58) Field of Classification Search
CPC .................................................. C07C 201/12
See application file for complete search history.

(56) References Cited

U.S. PATENT DOCUMENTS 3,780,575 A   12/1973   Urbanosky
3,859,851 A    1/1975   Urbanosky
(Continued)

FOREIGN PATENT DOCUMENTS

JP        07188129 A    7/1995
WO     2004063743 A1    7/2004
(Continued)

OTHER PUBLICATIONS

Bahr, el al., "Functionalization of Carbon Nanotubes by Electrochemical Reduction of Aryl Diazonium Salts: A Bucky Paper Electrode", 2001, Journal of the American Chemical Society, vol. 123, pp. 6536-6542.*

(Continued)

*Primary Examiner* — Jill Warden
*Assistant Examiner* — Matthew Krcha

(57) ABSTRACT

Derivatization of an elemental carbon surface is accomplished by exposing the carbon surface to an aprotic solvent containing a hydrazone molecule of formula (I) or the corresponding salt of formula (II) wherein $R_1$ is an organic group, and $R_2$ is an organic group or hydrogen and decomposing the hydrazone in the presence of elemental carbon to create a carbene moiety of formula (III): which attaches to the carbon surface. The attached groups may be redox active so that the derivatized carbon may be used in an electrochemical sensor.

(Continued)

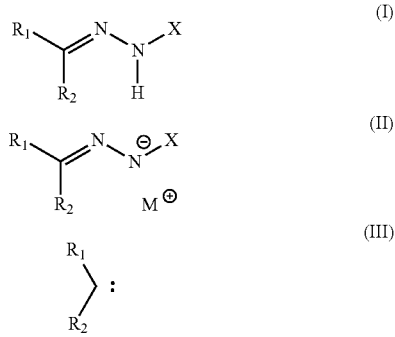

15 Claims, 3 Drawing Sheets

(51) Int. Cl.
C01B 31/02 (2006.01)
H01G 11/32 (2013.01)
H01M 4/583 (2010.01)
H01M 4/96 (2006.01)
B82Y 30/00 (2011.01)
B82Y 40/00 (2011.01)
G01N 27/30 (2006.01)

(52) U.S. Cl.
CPC .......... C01B 31/0273 (2013.01); C01B 31/04 (2013.01); C01B 31/0484 (2013.01); G01N 27/302 (2013.01); G01N 27/308 (2013.01); H01G 11/32 (2013.01); H01M 4/583 (2013.01); H01M 4/96 (2013.01); Y02E 60/13 (2013.01)

(56) References Cited

U.S. PATENT DOCUMENTS

| 4,994,671 | A | 2/1991 | Safinya et al. |
| 7,939,581 | B2 | 5/2011 | Moloney et al. |
| 2004/0223900 | A1 | 11/2004 | Khabashesku et al. |
| 2008/0063587 | A1 | 3/2008 | Strano et al. |
| 2008/0105852 | A1 | 5/2008 | Gaudiana et al. |
| 2009/0178921 | A1 | 7/2009 | Lawrence et al. |

FOREIGN PATENT DOCUMENTS

| WO | 2005066618 A1 | 7/2005 |
| WO | 2008006071 A2 | 1/2008 |
| WO | 2010001082 A1 | 1/2010 |
| WO | 2010106404 A2 | 9/2010 |
| WO | 2011010526 A1 | 1/2011 |

OTHER PUBLICATIONS

Aggarwal, et al., "A New Protocol for the In Situ Generation of Aromatic, Heteroaromatic, and Unsaturated Diazo Compounds and Its Application in Catalytic and Asymmetric Epoxidation of Carbonyl Compounds. Extensive Studies to Map Out Scope and Limitations, and Rationalization", Journal of the American Chemical Society, vol. 125, No. 36, 2003, pp. 10926-10940.

Baughman, et al., "Carbon nanotube actuators", Science, vol. 284, No. 5418, May 1999, pp. 1340-1344.

Calvert, "Nanotube composites: A recipe for strength", Nature, vol. 399, No. 6733, May 20, 1999, p. 210.

Campidelli, et al., "Functionalization of Carbon Nanotubes for Nanoelectronic and Photovoltaic Applications", John Wiley & Sons, Ltd., Chichester, West Sussex, United Kingdom, 2010, pp. 33-364.

Che, et al., "Carbon nanotubule membranes for electrochemical energy storage and production", Nature, vol. 393, No. 6683, May 28, 1998, pp. 346-348.

Cochet, et al., "Synthesis of a new polyaniline/anotube composite: "in-situ" polymerisation and charge transfer through site-selective interaction", Chemical Communications, vol. 16, 2001, pp. 1450-1451.

Collins, et al., "Nanotube Nanodevice", Science, vol. 278, Oct. 3, 1997, pp. 100-102.

De Heer, et al., "A Carbon Nanotube Field-Emission Electron Source", Science, vol. 270, Nov. 17, 1995, pp. 1179-1180.

Downard, "Electrochemically Assisted Covalent Modification of Carbon Electrodes", Electroanaysis, vol. 12, No. 14, 2000, pp. 1085-1096.

Fan, et al., "Synthesis, characterizations, and physical properties of carbon nanotubes coated by conducting polypyrrole", Journal of Applied Polymer Science, vol. 74, No. 11, Dec. 9, 1999, pp. 2605-2610.

Gebhardt, et al., "A Novel Diameter-Selective Functionalization of SWCNTs with Lithium Alkynylides", European Journal of Organic Chemistry, vol. 2010, Issue 8, Jan. 29, 2010, pp. 1494-1501.

Graupner, et al., "Chapter 16: Functionalization of Single-Walled Carbon Nanotubes: Chemistry and Characterization", Oxford Handbook of Nanoscience and Technology, vol. 1, 2010, p. 508.

Graupner, et al., "Nucleophilic-Alkylation-Reoxidation: A Functionalization Sequence for Single-Wall Carbon Nanotubes", Journal of the American Chemical Society, vol. 128, Issue 20, May 2, 2006, pp. 6683-6689.

Hauke, et al., "Chapter 6: Covalent Functionalization of Carbon Nanotubes", Carbon Nanotubes and related Structures—Synthesis, Characterization, Functionalization, and Applications, 2010, p. 135.

Hirsch, et al., "Chapter 1. Functionalization of Carbon Nanotubes", Functional Organic Materials: Syntheses, Strategies and Applications, Wiley-VCH Verlag GmbH & Co. KGaA, Weinheim, Germany, Jan. 16, 2007.

Iijima, et al., "Single-shell carbon nanotubes of 1-nm diameter", Nature, vol. 363, No. 6430, Jun. 17, 1993, pp. 603-604.

Jin, et al., "Novel conjugated polymers employing the binding of polyfluorene derivatives and C60", Synthetic Metals, vol. 159, Issues 15-16, Aug. 2009, pp. 1529-1537.

Kanungo, et al., "Suppression of Metallic Conductivity of Single-Walled Carbon Nanotubes by Cycloaddition Reactions", Science, vol. 323, No. 5911, Jan. 2009, pp. 234-237.

Kong, et al., "Controlled Functionalization of Multiwalled Carbon Nanotubes by in Situ Atom Transfer Radical Polymerization", Journal of the American Chemical Society, vol. 126, No. 2, Dec. 24, 2003, pp. 412-413.

Kroto, et al., "C60: Buckminsterfullerene", Nature, vol. 318, Nov. 14, 1985, pp. 162-163.

Lawrence, "Amperometric Detection of Sulfide: An Electrocatalytic Reaction with Ferrocene Carboxylate", Electroanalysis, vol. 18, Issue 17, Sep. 2006, pp. 1658-1663.

Liu, et al., "Fullerene Pipes", Science, vol. 280, 1998, pp. 1253-1256.

Liu, et al., "Preparing a Styrenic Polymer Composite Containing Well-Dispersed Carbon Nanotubes: Anionic Polymerization of a Nanotube-Bound p-Methylstyrene", Macromolecules, vol. 37, No. 2, 2004, pp. 283-287.

McCarthy, et al., "Microscopy studies of nanotube-conjugated polymer interactions", Synthetic Metals, vol. 121, Mar. 15, 2001, pp. 1225-1226.

Mi, et al., "Synthesis and characterization of a novel fullerene derivative for use in organic solar cells", Solar Energy Materials and Solar Cells, vol. 95, Issue 4, Apr. 4, 2011, pp. 1182-1187.

Modi, et al., "Miniaturized gas ionization sensors using carbon nanotubes", Letters to Nature, Nature, vol. 424, Jul. 10, 2003, pp. 171-174.

(56) References Cited

OTHER PUBLICATIONS

Moriwak, et al., "Synthesis and properties of novel methanofullerenes having ethylthienyl and/or n-pentyl group for photovoltaic cells", Tetrahedron, vol. 66, Issue 36, Sep. 4, 2010, pp. 7316-7321.
O'Connell, et al., "Reversible water-solubilization of single-walled carbon nanotubes by polymer wrapping", Chemical Physics Letters, vol. 342, Issues 3-4, Jul. 13, 2001, pp. 265-271.
Pan, et al., "Very long carbon nanotubes", Nature, vol. 394, No. 6694, Aug. 13, 1998, pp. 631-632.
Pandurangappa, et al., "Physical adsorption of N,N'-diphenyl-p-phenylenediamine onto carbon particles: Application to the detection of sulfide", Analyst, vol. 128, 2003, pp. 473-479.
Peng, et al., "Functional Covalent Chemistry of Carbon nanotube Surfaces", Advanced Materials, vol. 21, Issue 6, Feb. 9, 2009, pp. 625-642.
Qin, et al., "Polymer Brushes on Single-Walled Carbon Nanotubes by Atom Transfer Radical Polymerization of n-Butyl Methacrylate", Journal of the American Chemical Society, vol. 126, No. 1, Dec. 10, 2003, pp. 170-176.
Riggs, et al., "Optical Limiting Properties of Suspended and Solubilized Carbon Nanotubes", The Journal of Physical Chemistry B, vol. 104, No. 30, 2000, pp. 7071-7076.
Singh, et al., "Organic functionalisation and characterisation of single-walled carbon nanotubes", Chemical Society Reviews, vol. 38, 2009, pp. 2214-2230.
Syrgiannis, et al., "Covalent Sidewall Functionalization of SWNTs by Nucleophilic Addition of Lithium Amides", European Journal of Organic Chemistry, vol. 2008, No. 15, May 2008, pp. 2544-2550.
Tasis, et al., "Chemistry of Carbon Nanotubes", Chemical Society Reviews, vol. 106, 2006, pp. 1105-1136.
Viswanathan, et al., "Single-Step in Situ Synthesis of Polymer-Grafted Single-Wall Nanotube Composites", Journal of the American Chemical Society, vol. 125, No. 31, 2003, pp. 9258-9259.
Wang, et al., "Chemical Functionalization of Diamond Surfaces by Reaction with Diaryl Carbenes", Langmuir, vol. 24, No. 3, 2008, pp. 862-868.
Wildgoose, et al., "Chemically Modified Carbon Nanotubes for Use in Electroanalysis", Microchimica Acta, vol. 152, No. 3, 2006, pp. 187-214.
Wong, et al., "Covalently functionalized nanotubes as nanometre-sized probes in chemistry and biology", Nature, vol. 394, Jul. 2, 1998, pp. 52-55.
Wunderlich, et al., "Preferred Functionalization of Metallic and Small-Diameter Single-Walled Carbon Nanotubes by Nucleophilic Addition of Organolithium and -Magnesium Compounds Followed by Reoxidation", Chemistry—A European Journal, vol. 14, No. 5, Feb. 8, 2008, pp. 1607-1614.
Yao, et al., "Polymerization from the Surface of Single-Walled Carbon Nanotubes—Preparation and Characterization of Nanocomposites", Journal of the American Chemical Society, vol. 125, Issue 51, Dec. 2, 2003, pp. 16015-16024.
Zheng, et al., "Synthesis of C60 derivatives for polymer photovoltaic cell", Institute of Polymer Optoelectronic Materials and Devices, South China University of Technology, Guangzhou 510640, vol. 135-136, 2003, pp. 827-828.
Leventis, et al., "Derivatised carbon powder electrodes: reagentless pH sensors", Talanta, vol. 63, Issue 4, Jul. 8, 2004, pp. 1039-1051.
Banerjee, et al. "Covalent surface chemistry of single-walled carbon nanotubes", 2005, Advanced Materials, 17(1), pp. 17-29.
Fulton, et al. "The Use of Tosylhydrazone Salts as a Safe Alternative for Handling Diazo Compounds and Their Applications in Organic Synthesis", 2005, Eur. J. Org. Chem., vol. 8, pp. 1479-1492.

* cited by examiner

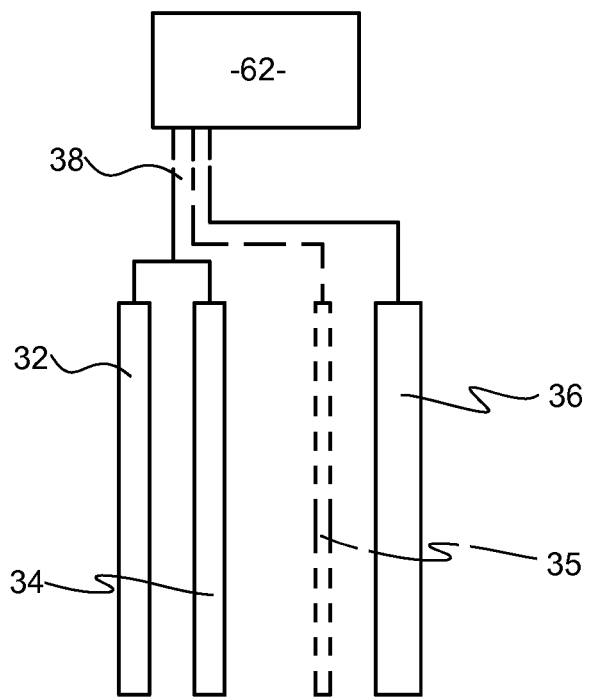
Fig 1
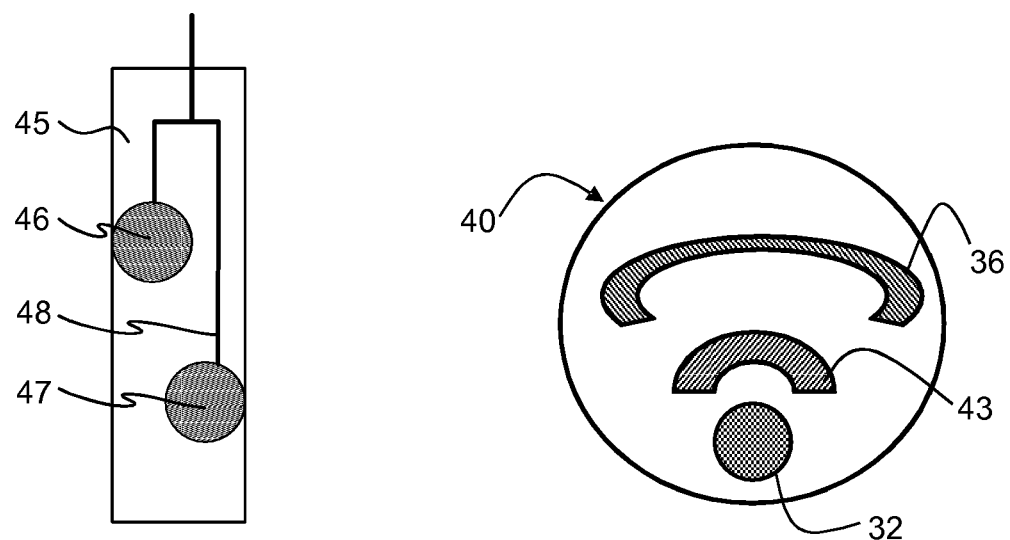
Fig 2
Fig 3

DERIVATIZATION OF CARBON

CROSS-REFERENCE TO RELATED APPLICATIONS

This application claims priority as a 35 USC 371 application to PCT application PCT/IB2012/057619 filed 21 Dec. 2012 which claims priority to GB application 1122050.6 filed 21 Dec. 2011. The disclosures of both applications above are incorporated by reference herein in their entireties.

BACKGROUND

Derivatization of carbon surfaces, i.e. the covalent attachment of molecules to the surface of elemental carbon, has attracted considerable interest in recent years, in particular in connection with attaching molecules to carbon nanotubes.

The derivatization of carbon may be carried out for a range of purposes which include modification of the surface properties of a carbon substrate, preparation of carbon-epoxy composites and attaching a molecule to a carbon electrode so that it can take part in an electrochemical reaction in an electrochemical sensor or an electrochemical catalyst.

Traditionally, carbon surfaces were modified by vigorous oxidation on the surface leading to the formation of carboxylic, quinonic, ketonic or hydroxylic groups, which were then reacted further with the target molecule. This aggressive process was difficult to control.

A number of procedures have been described for electrochemical induced derivatization leading to the formation of a single covalent bond between a carbon electrode and a moiety which becomes attached.

There have also been a number of disclosures of routes for derivatization of carbon, without electrochemistry. These include the homogeneous reduction of diazonium compounds in reducing media—see Pandurangappa et al Analyst, vol 127, page 1568 (2002) and Leventis et al, Talanta vol 63, page 1039 (2004). Also in this category is WO2005/066618 (Schlumberger) which describes the diazocoupling of anthraquinonyl and nitrophenyl groups onto carbon nanotubes by means of the reduction of diazonium salts. WO2010/106404 teaches exposing the carbon to a reaction mixture in which a reactive carbene is transiently formed by reaction between a precursor and an extremely strong base.

SUMMARY

This summary is provided to introduce a selection of concepts that are further described below. This summary is not intended to be used as an aid in limiting the scope of the subject matter claimed.

Disclosed here, in a first aspect, is a process for derivatization of an elemental carbon surface comprises exposing the carbon surface to an aprotic solvent containing a hydrazone molecule of the general formula

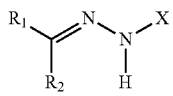

or the corresponding salt of formula

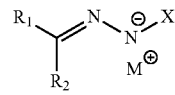

and decomposing the hydrazone. The aprotic solvent may be anhydrous.

When decomposition of the hydrazone occurs, nitrogen is released and a reactive carbene moiety of the structure:

is formed and becomes covalently attached to the carbon surface.

The groups $R_1$ and $R_2$ which become attached to the carbon surface may be the same or different. They may be aliphatic, aromatic or have both aliphatic and aromatic parts. $R_2$ (but not $R_1$) may simply be hydrogen. The group X may be a group recognised to be a good leaving group such as an aryl sulfonyl group.

Embodiments of the process have the advantage that the reaction conditions can be mild and that the reaction mixture remains a mobile fluid as reaction takes place. It is possible to use a range of groups $R_1$ and $R_2$ which become attached to the elemental carbon surface. The reaction may be used to derivatize various forms of elemental carbon in solid form, which may be particulate solid carbon, including graphite and carbon nanotubes which may then be immobilised on electrodes. It is also possible to carry out the reaction directly onto carbon electrodes.

Within the broad range of possibilities, the groups which are attached to carbon may be aromatic quinones or aromatic nitro compounds which have previously been disclosed for use in electrochemical sensors. It is also possible by means of the present derivatization reaction to attach a moiety containing ferrocene to act as a reference or to take part in reaction.

So another aspect of the subject matter disclosed by this application provides an electrochemical sensor electrode comprising elemental carbon having one or more redox-active groups attached thereto by the process above. Such a sensor may be a constituent part of measuring apparatus which also has means to apply voltage to the electrode and measure current flow.

Such apparatus may be used for determining presence or concentration of an analyte, and in a further aspect the subject matter disclosed herein provides a method of determining presence or concentration of an analyte in a liquid, comprising contacting the liquid with at least two electrodes, at least one of which is an electrode comprising elemental carbon having a redox-active group covalently attached thereto through a process as above and carrying out electrochemical measurement with the electrodes. The liquid which contains the analyte may be an aqueous solution but it may also be a non-aqueous liquid such as acetonitrile. A method of determining analyte concentration may comprise applying a potential to the sensor electrode(s) in a sweep over a range sufficient to bring about at least one oxidation and/or reduction of the redox active compound; measuring potential or potentials corresponding to one or more said oxidation and/or reductions; and then processing the measurements to give a determination of analyte concentration.

BRIEF DESCRIPTION OF THE DRAWINGS

FIG. 1 is a diagrammatic illustration of the parts of an electrochemical sensor;

FIG. 2 shows another electrode construction;

FIG. 3 illustrates the geometrical surface layout of the surface of a sensor;

DETAILED DESCRIPTION

Figure 4:
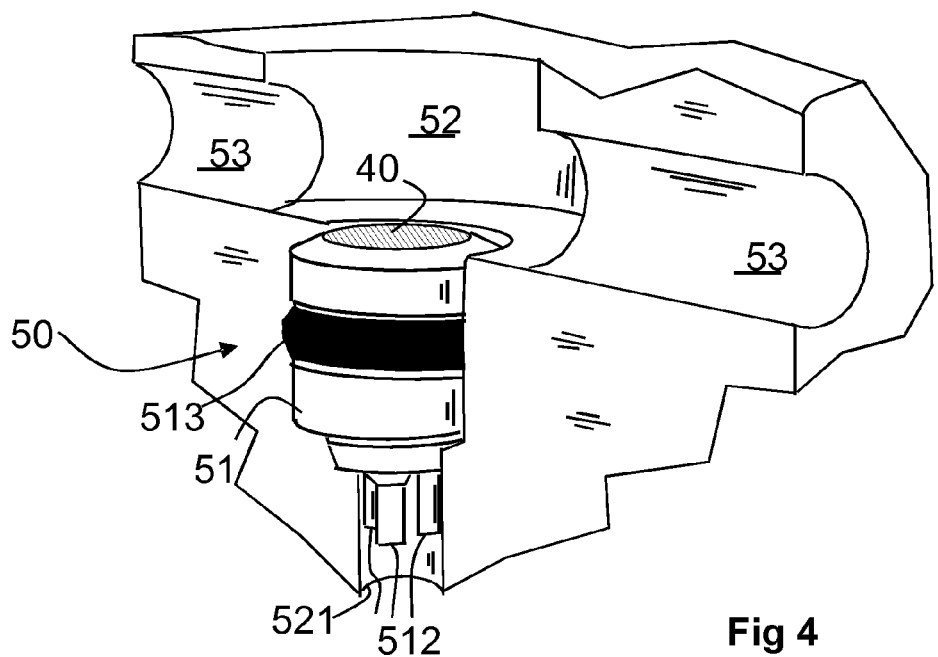
FIG. 4 is a perspective view, partially cut-away, of an electrochemical sensor incorporating the surface of FIG. 3.

A hydrazone which may be in salt form with the general formula

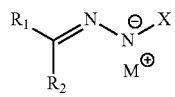

is made to decompose into nitrogen, a carbene $R_1R_2C$: which becomes attached to an elemental carbon surface, and a leaving group $X^-$. In the general formula given above, X denotes a group which leaves as $X^-$ when a covalent sigma bond to nitrogen is broken. The term "leaving group" is customarily used in the context of a substitution reaction whereas the reaction here is a decomposition. However, in some embodiments the group X may have characteristics of a good leaving group and it may be a sulfonyl group of the formula $—SO_2—Y$.

Formation of a carbene from a tosylhydrazone (in which group Y is paratoluene sulfonyl) is known as the Bamford-Stevens reaction and the mechanism of the reaction is

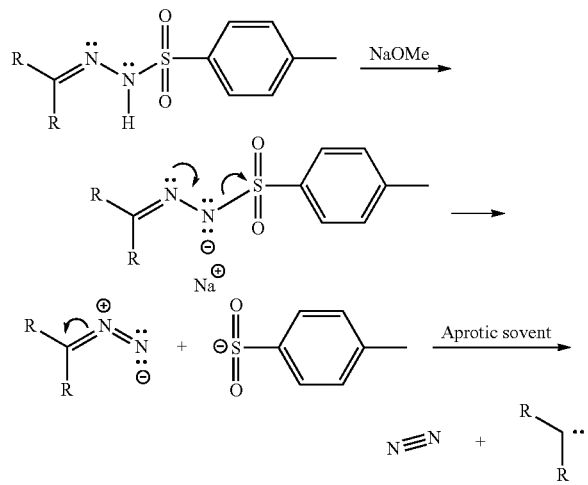

The group Y may be an aromatic group bearing one or more substituents such as a phenyl or naphthyl group bearing one or more alkyl substituents. The $—SO_2—Y$ moiety may be a para-toluene sulphonyl group (customarily referred to as a tosyl) group but it may also be other sulphonyl groups such as a xylyl sulfonyl or methylnapthylsulphonyl group.

Further possibilities are that the group Y is an alkyl group, a fluorine atom or a fluorinated alkyl group.

There are a range of possibilities for the $R_1$ and $R_2$ groups which form the $R_1R_2C$: carbene and become attached to an elemental carbon surface. $R_2$ may be hydrogen so that the carbene which becomes attached to the carbon surface is $R_1CH$: In some embodiments the $R_1$ group and possibly also the $R_2$ group comprises an aromatic group such that the carbon atom of the $>C=N—N<$ hydrazone group (which becomes the reactive carbon atom of the carbene and directly attached to the carbon surface) can form delocalised bonds with the aromatic ring.

For instance $R_1$ may comprise a phenyl group, a condensed aromatic ring system such as napthyl or anthracenyl or an aromatic ring connected to a vinyl group such as a styryl group. An aromatic group may include one or more hetero atoms and thus be a heterocyclic group or a condensed heterocyclic group.

The $R_1$ group and possibly also the $R_2$ group may comprise one or more substituents capable of undergoing an electrochemical redox reaction, and more specifically the $R_1$ group and possibly also the $R_2$ group may comprise an aromatic ring or system bearing one or more such substituents which are functional groups able to undergo electrochemical redox reaction, such as a nitro group or two keto groups as in a quinone. Aromatic compounds which have two groups convertible between a reduced hydroxyl form and an oxidised keto form by a two electron, two proton reaction have been previously been found to be particularly suitable as pH sensitive redox active species: anthraquinone is a common example.

Use of a nitro-substituted aromatic moiety as precursor of a redox-active compound was disclosed in WO2010/001082. By application of sufficient voltage some of the nitro groups can be irreversibly reduced electrochemically to hydroxylamino or nitroso groups after which the reduced group displays a pH sensitive reversible redox conversion between a hydroxylamino group and a nitroso group. In the event that this nitroso-/hydroxylamino-substituted moiety becomes depleted while some of its nitro substituted precursor remains available, a voltage pulse can be applied to bring about irreversible reduction of some more of the nitro-substituted precursor.

One possibility is that a group $R_1$ may comprise a ferrocenyl group, which is a group capable of undergoing redox reaction as has been pointed out in WO2005/66618 and elsewhere. Embodiments of such an $R_1$ group may comprise an aromatic ring with a ferrocenyl or substituted ferrocenyl group attached as a substituent on the aromatic ring.

Embodiments of the process may serve to immobilise redox active groups onto elemental carbon which is then used to provide an electrode for electrochemical reaction or in an electrochemical sensor.

The hydrazone of general formula

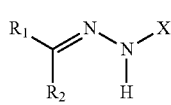

may conveniently be made by condensation of an aldehyde of the formula $R_1R_2CHO$ and a hydrazide of the formula $H_2N-NH-X$. The condensation reaction will generally be followed by conversion of the hydrazone into salt form, by reaction with a base such as sodium methoxide. Procedures for such a preparation have been described in the literature, for instance Aggarwal et al J. Amer. Chem. Soc vol 125, p 10926 (2003) and Fulton et al Eur. J. Org. Chem. Vol 8 pp 1479-92 (2005).

Decomposition of the hydrazone to bring about carbene formation and derivatization of carbon may done in several ways. One possibility is to supply energy to the reaction mixture by heating it. Another is to supply energy by irradiating with ultra-violet light and so causing photolytic decomposition. A further possibility is to add a catalyst for the decomposition reaction.

The relative ratio of the elemental carbon substrate and the hydrazone providing the carbene which is to be attached to it may vary considerably. The amount of the hydrazone may be much less than the theoretical amount required to attach to all possible binding sites on the surface of the elemental carbon.

The elemental carbon may have a variety of forms including graphite powder, glassy carbon, carbon fibres, carbon black or carbon paste, boron doped diamond and carbon epoxy. A further form of carbon which may be derivatized is the carbon nanotube (CNT) which was discovered in 1991. The structure of carbon nanotubes approximates to rolled-up sheets of graphite and can be formed as either single or multi-walled tubes. Single-walled carbon nanotubes (SWCNTs) constitute a single, hollow graphite tube. Multi-walled carbon nanotubes (MWCNTs) on the other hand consist of several concentric tubes fitted one inside the other. Yet another form of carbon which may be derivatized is graphene which may be in the form of graphene flakes and after derivitization these may be immobilized on a conductive substrate. All of these forms of carbon are in a solid form, which may be a particulate solid form, or contain carbon in a solid form.

The elemental carbon may be conductive and may be for use in an electrode. Forms of conducting carbon used in electrode manufacture are glassy carbon, carbon fibres, carbon black, various forms of graphite, carbon paste, boron doped diamond and carbon epoxy. Carbon nanotubes may also be used as part of an electrode and may be immobilized on the surface of another form of conducting carbon.

Elemental carbon which has been derivatised by the attachment of a molecular species as described above may be used for a variety of purposes. In particular, the $R_1R_2C$: or $R_1CH$: carbene moiety which becomes attached to carbon may be such that it can undergo electrochemical reduction or oxidation, so that the derivatised carbon can be used in an electrochemical sensor, for example in the manner described in WO 2005/66618, the disclosure of which is incorporated herein by reference. A reversible oxidation and reduction which can be monitored by voltammetry is particularly useful. This may be preceded by an initial irreversible alteration of the covalently attached moiety to form a species which is still covalently attached to the carbon substrate and can undergo reversible electrochemical reduction and oxidation.

Embodiments of the derivatization process will now be described with reference to the accompanying drawings and the following examples.

EXAMPLE 1

A hydrazone (13) containing a toluenesulfonyl leaving group was prepared, then converted to the corresponding sodium salt (14) with sodium methoxide and decomposed by heating in the presence of graphite to functionalise the graphite (15) with para nitrophenyl groups. The reaction scheme is:

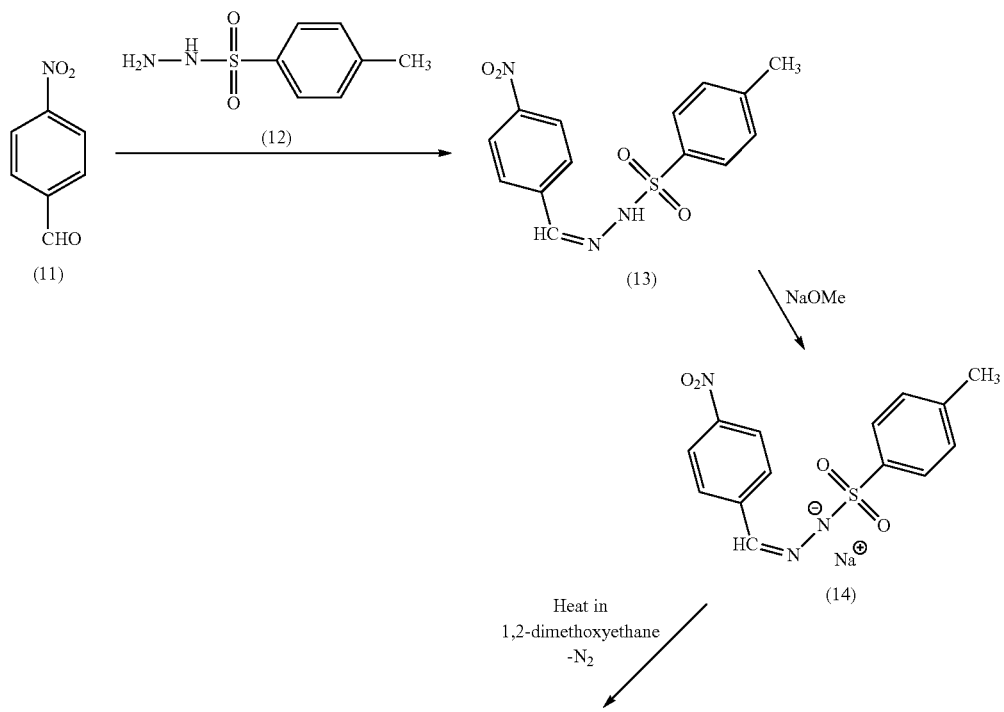

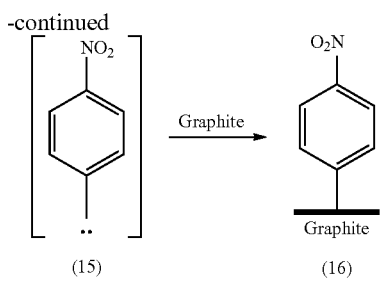

As illustrated by the top row of the reaction scheme above, the first step was synthesis of the hydrazone 4-methyl-N-[(4-nitrophenyl)methyleneamino]benzene sulfonamide (13).

para-Toluenesulfonyl hydrazide (12) (3.1 g, 16.6 mmol) was suspended in anhydrous methanol (15 ml) and 4-nitrobenzaldehyde (11) (2.25 g, 14.9 mmol) was added over approximately 1 minute; the hydrazide began to go into solution and the product began to precipitate. The suspension was stirred at ambient temperature for 2 hours, the solid was collected by filtration and washed with methanol, followed by drying at ambient temperature, under vacuum, overnight to give the hydrazone, 4-methyl-N-[(4-nitrophenyl)methyleneamino]benzene sulfonamide (13), 3.4 g (71%). Peaks observed using nmr were $^1$H NMR (CDCl$_3$, 400 MHz) δ=2.45 (s 3H), 7.38 (d 2H J=8 Hz), 7.79 (d 2H J=8 Hz), 7.85 (s 1H), 7.93 (d 2H J=8 Hz), 8.25 (d 2H J=8 Hz).

To form its sodium salt, 4-methyl-N-[(4-nitrophenyl) methyleneamino]benzene sulfonamide (13) (514 mg, 1.68 mmol) was suspended in anhydrous methanol (3 ml) and a solution of sodium methoxide (87 mg, 1.61 mmol) in methanol (2 ml) was added and the solution stirred at ambient temperature for 1 hour. The solvent was reduced to low volume, anhydrous diethyl ether added and the resultant solid, which was the salt, sodium [(4-nitrophenyl)methyleneamino]-(p-tolylsulfonyl)azanide (14), was filtered and washed with anhydrous diethyl ether. in the immobilisation stage.

The sodium salt (14), prepared above, was immediately immobilized onto graphite. The salt (14) was added to a suspension of graphite (52 mg) in anhydrous dimethoxyethane (5 ml) and heated at 65° C. for 1.5 hour then at 85° C. for 1.5 hour. The suspension was cooled, water added and the functionalized graphite collected by centrifugation. The derivatised graphite (16) was washed sequentially with water, dimethylformamide, water and methanol and then dried under vacuum at ambient temperature.

EXAMPLE 2

The functionalized graphite prepared in Example 1 was examined electrochemically to confirm that the functionalizing groups were present on the graphite. The functionalized graphite was first dispersed in dichloromethane at a concentration of 1 mg/mL. A 20 μL aliquot of the resulting dispersion was then spread on the surface of a glassy carbon electrode and allowed to dry in ambient air. Once dried the electrode was placed in a pH 7 phosphate buffer along with a saturated calomel electrode as reference electrode and a platinum counter electrode, thus forming a three electrode electrochemical cell. Cyclic voltammetry was carried out using a PGSTAT 30 potentiostat (Ecochemie, Netherlands).

The resulting voltammogram showed an initial reduction wave at +0.8 V for irreversible reduction of the nitro group to a hydroxylamine group. Subsequent cycles showed the emergence of a new reduction and oxidation waves at +0.0 V attributed to the reversible reduction of the hydroxylamine group to the nitroso moiety. This is consistent with reported results for voltammetry of a nitrophenyl group and confirms that the procedure of Example 1 had immobilized the nitrophenyl groups onto the graphite.

EXAMPLE 3

4-Methyl-N-[(3-ferrocenylphenyl)methyleneamino]benzenesulfonamide which is a hydrazone with a ferrocenyl group as a substituent was synthesised by a two-stage route then converted to the corresponding sodium salt and decomposed by heating in the presence of graphite to functionalise the graphite with ferrocenyl groups, as illustrated by the following reaction scheme:

The first stage was synthesis of 3-ferrocenylbenzaldehyde (23) thus:

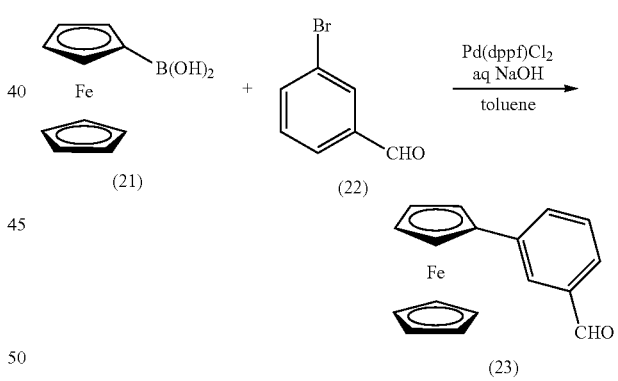

Ferrocene boronic acid (21) (7.25 g, 25 mmol) and 3-bromobenzaldehyde (22) (3.85 g, 20.8 mmol) were added to toluene (185 ml/5M NaOH 15 ml) and the mixture was purged with nitrogen for 10 minutes.

1',1-Bis(diphenylphosphino)ferrocene]dichloropalladium (II) complex with dichloromethane (1.25 g) was added and the mixture heated at 85-90° C. for 3.5 hours and then left to stand at ambient temperature overnight. The solvent was removed and the residue washed with toluene. The combined solvent was evaporated, the residue dissolved in dichloromethane and absorbed onto silica. The silica was applied to a silica column and eluted with 2-5% ethyl acetate/hexane to give 3-ferrocenylbenzaldehyde (23), 3.47 g (57%). Peaks observed using nmr were: $^1$H NMR (400 MHz, CDCl$_3$) δ=4.09 (s, 5H), 4.37 (t, 2H, J=1.88 Hz), 4.71

(t, 2 Hz, J=1.88 Hz), 7.46 (t, 1H), 7.69 (bd, 1H J=7.6 Hz), 7.73 (bd, 1H J=7.6 Hz), 8.00 (bs, 1H), 10.08 (s, 1H) and $^{13}$C NMR (100 MHz, CDCl$_3$) δ=66.66, 69.53, 69.73, 83.56, 126.40, 127.66, 129.07, 131.91, 136.66, 140.94, 192.57

The next stage was conversion of 3-ferrocenylbenzaldehyde (23) to 4-Methyl-N-[(3-ferrocenylphenyl)methyleneamino]benzenesulfonamide (24) thus:

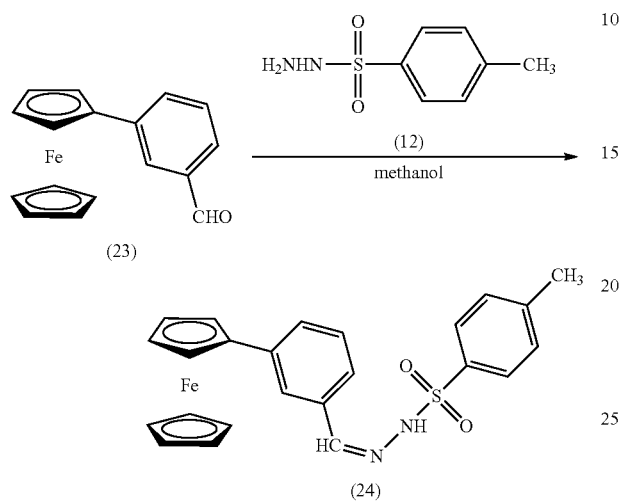

para-Toluenesulfonyl hydrazide (12) (250 mg, 1.34 mmol) was suspended in anhydrous methanol (0.5 ml) and 3-ferrocenylbenzaldehyde (3) (348 mg, 1.2 mmol) was added over a time of about one minute after which the hydrazide began to go into solution and the product began to precipitate; methanol (0.3 ml) was added to aid stirring. The suspension was stirred at ambient temperature for 40 minutes. Hexane was added, the solid collected by filtration, washed with cold methanol and dried at ambient temperature, under vacuum, to give 4-methyl-N-[(3-ferrocenylphenyl)methyleneamino]benzene sulfonamide (24), 509 mg, 92% yield. Peaks observed by nmr were $^1$H NMR (400 MHz, CDCl$_3$) δ=2.44 (s, 3H), 4.07 (s, 5H), 4.38 (t, 2H) 4.69 (t, 2H), 7.33 (d, 1H J=6 Hz), 7.36 (d, 1H, J=8 Hz), 7 42 (bd, 1H J=7.7 Hz), 7.52 (bd, 1H J=7.7 Hz), 7.71 (bs, 1H), 7.81 (s, 1H), 7.90 (s, 1H), 7.94 (d, 2H J=8.3 Hz)

The hydrazone was converted to its sodium salt and immobilized on graphite, thus:

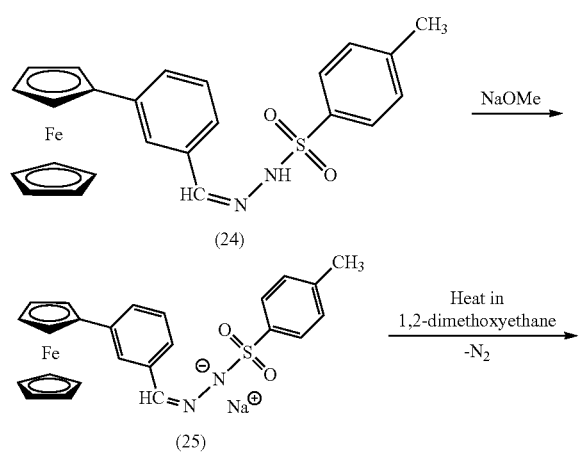

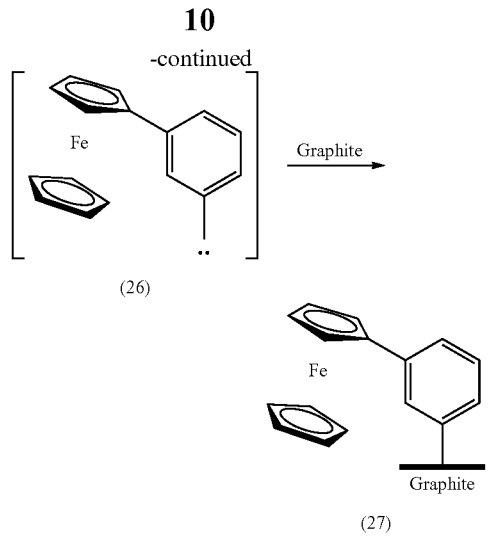

4-Methyl-N-[(3-ferrocenylphenyl)methyleneamino]benzenesulfonamide (24) (492 mg, 1.07 mmol) was suspended in anhydrous methanol (1 ml) and a solution of sodium methoxide (58 mg, 1.07 mmol) in methanol (0.5 ml) was added and the solution stirred at ambient temperature for 40 minutes. The solvent was reduced by about ⅔, diethyl ether was added, and the precipitated solid salt, which was sodium [(3-ferrocenylphenyl)methyleneamino]-(p-tolylsulfonyl) azanide (25) was filtered and washed with anhydrous diethyl ether. It was used immediately in the immobilisation stage.

The sodium salt (25), prepared above, was at once added to a suspension of graphite (35 mg) in anhydrous dimethoxyethane (2 ml) and heated at 65° C. for 1.5 hours then at 85° C. for 1.5 hours whereupon the derivatised graphite (27) was collected by centrifugation. The derivatised graphite (27) was washed sequentially with methanol, water and again with methanol and then dried under vacuum at ambient temperature.

EXAMPLE 4

A carbon electrode bearing the derivatised graphite from Example 3 was prepared and used for cyclic voltammetry as in Example 2. The resulting voltammograms showed reduction and oxidation waves at the potentials expected for ferrocene confirming that the ferrocenylphenyl groups had been attached to the graphite.

Cyclic voltammetry was carried out every 30 minutes. The ferrocene redox waves decayed over time but about 12 hours elapsed before the redox could no longer be observed.

In a comparative experiment, ferrocenyl benzyl bromide was used to derivatize graphite powder by the procedure of WO2010/106404 in which 1,8-diazabicyclo[5.4.0]undec-7-ene (DBU) was used to generate the reactive carbene from the ferrocenyl benzyl bromide. A carbon electrode bearing the derivatised graphite was prepared and likewise used for cyclic voltammetry every 30 minutes. The ferrocene redox waves decayed and could no longer be observed after only 3 hours.

Elaborating further on the nature and function of redox-active compounds which may be immobilized on an electrode, there are a number of redox active compounds which are sensitive to pH, so that when observed by voltammetry, the voltage at which there is maximum current flow (ie the voltage of the peak of the voltammetric wave) is dependent on pH. An electrode with such a compound immobilised on it can be used as a pH sensor.

Aromatic quinones which have such redox reactions are disclosed in WO2005/066618. The use of aromatic nitrogen compounds, which undergo irreversible reduction to hydroxylamine and thereafter undergo pH dependent reversible oxidation from hydroxylamine to nitroso compounds are disclosed in WO2010/001082.

In contrast, the oxidative and reductive peaks for ferrocene are substantially independent of applied voltage, so an electrode with a ferrocene compound immobilised on it can serve as a reference when measuring pH, as mentioned in WO2005/066618. A compound which is sensitive to an analyte and a reference compound may be immobilised on the same electrode or on separate electrodes.

An electrochemical reaction of a redox active compound may couple to a reaction of an analyte species of interest and act as a catalyst for its reaction. This analyte species can be determined by means of an amperometric measurement to measure any increase in the electric current which flows when the species is present: the magnitude of the increase in current provides a measure of the concentration of the species of interest.

One instance of this is determination of oxygen. If oxygen is present in an aqueous electrolyte, the electrochemical reduction of a quinone can couple to the reduction of that oxygen to water. The quinone then serves as a catalyst in the electrochemical reduction of oxygen and the concentration of oxygen can be determined from the increase in electric current compared with the current which flows in the absence of oxygen. The reactions can be represented as

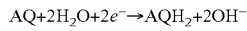

$$AQ+2H_2O+2e^- \rightarrow AQH_2+2OH^-$$

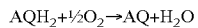

$$AQH_2+\tfrac{1}{2}O_2 \rightarrow AQ+H_2O$$

Under alkaline conditions, oxygen can be converted to hydrogen peroxide, the second step of the above reaction scheme then taking the form:

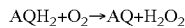

$$AQH_2+O_2 \rightarrow AQ+H_2O_2$$

If the electrochemical sensor is in contact with a non-aqueous liquid such as acetonitrile, the electrochemical reduction of a quinone can again couple to the reduction of oxygen, but the oxygen is reduced to superoxide, thus:

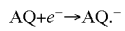

$$AQ+e^- \rightarrow AQ.^-$$

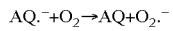

$$AQ.^-+O_2 \rightarrow AQ+O_2.^-$$

The redox reaction of ferrocene can couple to the oxidation of hydrogen sulphide to sulphur, so that the concentration of hydrogen sulphide can be determined from the increase in current compared to the current which flows in the absence of hydrogen sulphide. The use of ferrocene in the determination of hydrogen sulfide has been mentioned in WO2004/063743 and WO2010/001082. The reactions can be written as

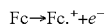

$$Fc \rightarrow Fc.^+ + e^-$$

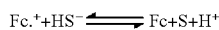

$$Fc.^+ + HS^- \rightleftharpoons Fc + S + H^+$$

Ferrocene compounds can also be used in the determination of other analytes, as mentioned by Lawrence in Electroanalysis vol 18 pp 1658-1663 (2006).

As mentioned above, the derivatization reaction can be used to immobilize a compound by covalent attachment directly onto a carbon electrode. Another possibility is to attach the compound to particulate carbon such as graphite powder or carbon nanotubes and then immobilize this derivatized carbon on a carbon electrode. This may be done, as in the examples above, by evaporation of a suspension of the particles in a volatile solvent.

Another possibility is to pack such derivatized particulate carbon into a recessed cavity in an electrode. The empty recess might be filled with the derivatized carbon powder which would be mechanically compacted. The resulting void in the recess would then be refilled and compacted again. This would be repeated several times until the recess is full. The material would be pressed such that the carbon particles are packed into a dense matrix.

A further possibility is that derivatized carbon particles may be screen printed onto a substrate which may be an insulating material. Carbon particles derivatized with a second redox active compound which is insensitive to analyte/pH and which acts as a reference may be screen printed onto the same or another substrate. The particulate carbon may be combined with a binding material, which may be a conductive binding material such as a graphite-containing ink, and then screen printed onto the electrode. An external reference electrode may possibly be used with such a screen-printed electrode. One possible external reference is a silver/silver-chloride electrode. A screen-printed electrode may possibly carry such an external reference electrode on a portion of an insulating substrate. Particulate carbon derivatized with a redox active compound, mixed with a binder may also be applied to a working electrode by an inkjet-type process as an alternative to screen printing.

A screen-printed electrode may possibly be covered with a polymer film or coating. The polymer film or coating may, among other things, make the electrode more robust, prevent external adverse effects of the redox active compound(s), and allow for sterilization of the electrode without affecting the functionality of the electrode.

Some embodiments of electrochemical sensor include a temperature probe for measuring a temperature of the fluid, wherein the temperature measurement may be used to calibrate the electrochemical sensor.

An electrochemical sensor could be incorporated into a wide variety of tools and equipment. Possibilities include use in tools which are located permanently downhole, use in tools which are conveyed downhole, for instance at the head of coiled tubing or by drillpipe or on a wireline, use in underground, undersea or surface pipeline equipment to monitor liquid flowing in the pipeline, and use in a wide variety of process plant at the Earth's surface, including use in water treatment.

FIG. 1 diagrammatically illustrates apparatus which may be used in pH measurement. A working electrode 32 has carbon particles derivatized with a pH-sensitive redox active compound immobilized on its surface. A reference electrode 34 has carbon particles derivatized with a ferrocene compound immobilized on its surface. There is also counter electrode 36. All the electrodes are connected by cable or other wiring indicated at 38 to a potentiostat 62 or other control unit which provides electric power and measurement. This arrangement avoids a need for a standard reference electrode such as a standard calomel electrode. However, another possibility would be to provide such a standard electrode, as shown by broken lines at 35 and possibly dispense with the ferrocene electrode 34. The various electrodes are immersed in or otherwise exposed to fluid whose pH is to be measured.

Measuring apparatus may comprise electrode(s) which utilize derivatized graphite and also a control unit providing both electrical power and measurement. A control unit such as 62 may comprise a power supply, voltage supply, potentiostat and/or the like for applying an electrical potential to the working electrode 32 and a detector, such as a voltmeter, a potentiometer, ammeter, resistometer or a circuit for measuring voltage and for current and converting to a digital output, for measuring a potential between the working electrode 32 and the counter electrode 36 and/or potential between the working electrode 32 and the reference electrode 34 or 35 and for measuring a current flowing between the working electrode 32 and the counter electrode 36 (where the current flow will change as a result of the oxidation/reduction of a redox species). The control unit may in particular be a potentiostat. Suitable potentiostats are available from Eco Chemie BV, Utrecht, Netherlands.

A control unit 62 which is a potentiostat may sweep a voltage difference across the electrodes and carry out voltammetry so that, for example, linear sweep voltammetry, cyclic voltammetry, or square wave voltammetry may be used to obtain measurements of the analyte using the electrochemical sensor. The control unit 62 may include signal processing electronics.

FIG. 2 shows a possible variation. A conductive paste containing carbon derivatized with a pH sensitive redox compound is printed on one area 46 of an insulating substrate 45 to provide an electrode 32. A second conductive paste containing carbon derivatized with a pH insensitive ferrocene compound is printed on an area 47 as a reference electrode and both areas 46,47 are connected together and connected to a cable 38 leading to a control unit by conductive tracks 48 on the substrate 45.

The electrodes 46, 47 may be screen printed using stencil designs to delineate the areas of the electrode. To form the working electrode, particulate carbon derivatized with a redox active compound may be mixed within a carbon-graphite ink and deposited on area 46 of a substrate 45 which may comprise polyester or other insulating polymer. To form the reference electrode a carbon-graphite ink may be deposited on area 47 of the substrate, then a reference electrode material, such as silver/silver-chloride may be deposited as a paste onto the area of deposited carbon. In some embodiments of electrode, a polymer coating may be applied on top of deposited materials (including deposited derivatized carbon). A polymer coating which is permeable to water and other small molecules may prevent derivatized carbon from becoming detached from the working electrode, but still allow for interactions between an analyte and a redox active compound on the working electrode. For example a polymer coating may comprise a polysulphone polymer or a polystyrene polymer.

FIG. 3 shows a possible geometric configuration or layout for the surface 40 of a sensor which is exposed to the fluid to be tested, which may, merely by way of example be a wellbore fluid. The surface includes a disk shaped working electrode 32, a second electrode 43, which may be a ferrocene electrode or an external reference electrode such as a silver/silver chloride electrode, and a counter electrode 36.

A schematic of a microsensor 50 incorporating such a surface is shown in FIG. 4. The body 51 of the sensor is fixed into the end section of an opening 52. The body carries the electrode surface 511 and contacts 512 that provide connection points to voltage supply and measurement through a small channel 521 at the bottom of the opening 52. A sealing ring 513 protects the contact points and electronics from the fluid to be tested that passes under operation conditions through the sample channel 53.

Figure 5:
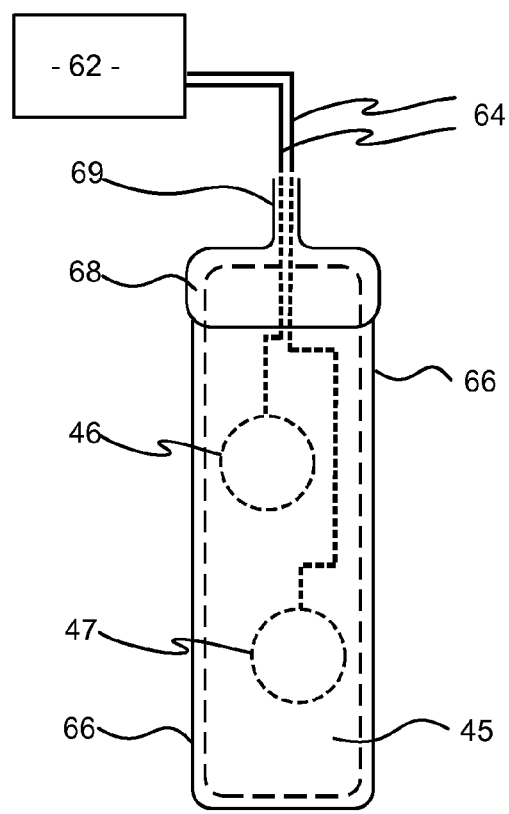
FIG. 5 illustrates a working electrode covered at least in part by a polymer layer.

FIG. 5 shows a substrate 45 carrying a working electrode on an area 46 and a reference electrode on an area 47. These are not connected together but are connected by separate conductors within a cable 64 to a potentiostat 62 which may be a handheld device. After deposition of electrode materials onto the substrate 45, the substrate and deposited materials were coated with a permeable polymer layer indicated by reference 66. Methods to deposit the polymer in a generally uniform layer include spin coating, dip coating and application using solvent evaporation. One end of the coated substrate has an impermeable covering 68 which merges with the sheath 69 of the cable 64.

Figure 6:
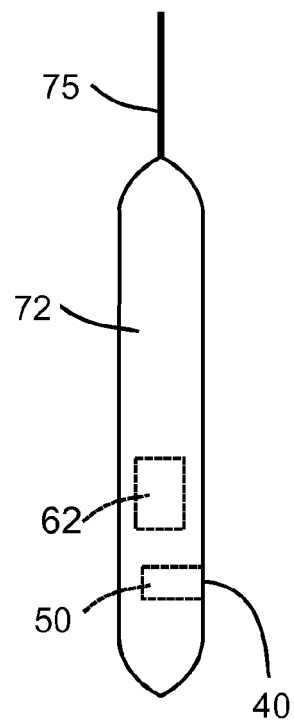
FIG. 6 is a diagrammatic illustration of a cable-suspended tool for testing water.

One application of an electrochemical sensor may lie in the monitoring of underground bodies of water for the purposes of resource management. Using monitoring wells drilled into the aquifers, one or more sensors may be deployed on a cable from the surface. The sensor(s) may be in place for a relatively short duration (as part of a logging operation) or a longer term (as part of a monitoring application). FIG. 6 illustrates a tool for investigating subterranean water. This tool has a cylindrical enclosure 72 which is suspended from a cable 75. A sensor unit such as the sensor 50 shown in FIG. 4 is accommodated within the enclosure 72 so that its surface 40 is exposed to the subterranean water. The tool also encloses also encloses a unit 62 for supplying voltage to the electrodes of the sensor 50, measuring the current which flows and transmitting the results to the surface.

The sensor may be a pH sensor. Suspending such a device on a cable within producing wells may provide information on produced water quality. Also, the pH sensor may be deployed in injection wells, e.g. when water is injected into an aquifer for later retrieval, where pH may be used to monitor the quality of the water being injected or retrieved.

Figure 7:
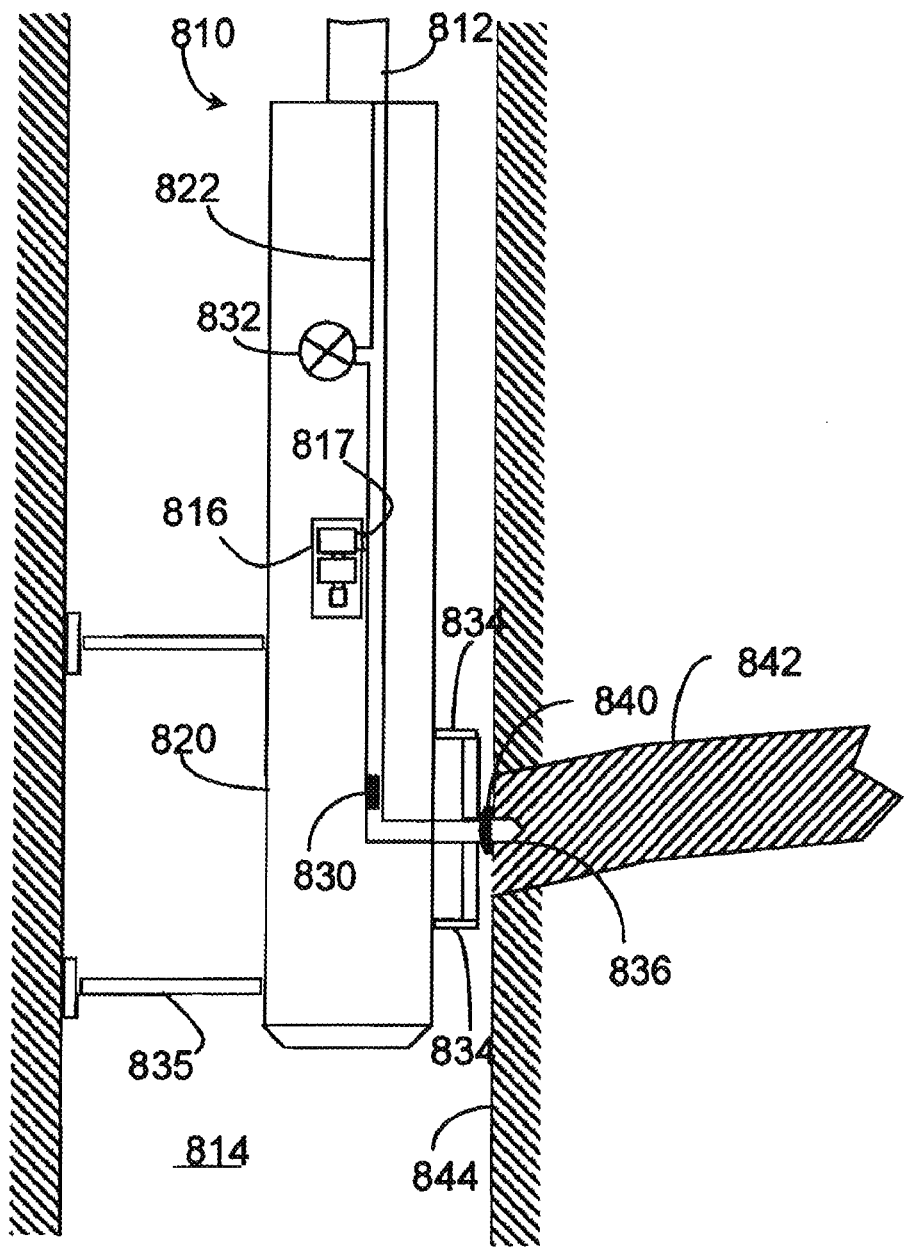
FIG. 7 illustrates an example of an electrochemical sensor as part of a wireline formation testing apparatus in a wellbore.

FIG. 7 shows a formation testing apparatus 810 held on a wireline 812 within a wellbore 814. The apparatus 810 is a well-known modular dynamic tester (MDT, Trade Mark of Schlumberger) as described in the co-owned U.S. Pat. No. 3,859,851 to Urbanosky, U.S. Pat. No. 3,780,575 to Urbanosky and U.S. Pat. No. 4,994,671 to Safinya et al., with this known tester being modified by introduction of an electrochemical analyzing sensor 816 substantially similar to sensor 50 of FIG. 4 The modular dynamics tester comprises body 820 approximately 30 m long and containing a main flowline bus or conduit 822. The analysing tool 816 communicates with the flowline 822 via opening 817. In addition to the novel sensor system 816, the testing apparatus comprises an optical fluid analyser 830 within the lower part of the flowline 822. The flow through the flowline 822 is driven by means of a pump 832 located towards the upper end of the flowline 822. Hydraulic arms 834 and counterarms 835 are attached external to the body 820 and carry a sample probe tip 836 for sampling fluid. The base of the probing tip 836 is isolated from the wellbore 814 by an o-ring 840, or other sealing devices, e.g. packers.

Before completion of a well, the modular dynamics tester is lowered into the well on the wireline 812. After reaching a target depth, i.e., the layer 842 of the formation which is to be sampled, the hydraulic arms 834 are extended to engage the sample probe tip 836 with the formation. The o-ring 840 at the base of the sample probe 836 forms a seal between the side of the wellbore 844 and the formation 842 into which the probe 836 is inserted and prevents the sample probe 836 from acquiring fluid directly from the borehole 814.

Once the sample probe 836 is inserted into the formation 842, an electrical signal is passed down the wireline 812 from the surface so as to start the pump 832 and the sensor systems 816 and 830 to begin sampling of a sample of fluid from the formation 842. The electrochemical sensor 816 can then measure the pH or concentration of another analyte such as hydrogen sulfide in the formation effluent.

While the preceding uses of an electrochemical sensor are in the hydrocarbon and water industries, embodiments of electrochemical sensor incorporating derivatized carbon may be used for detecting an analyte in a whole host of industries, including food processing, pharmaceutical, medical, water management and treatment, and biochemical industries, as well as research laboratories. A polymer coating may prevent escape of derivatized carbon particles from an electrode into the fluid around it, but still allow for interactions between an analyte and one or more redox active compounds on the electrode.

Derivatization of carbon may also be carried out for applications other than electrochemical sensors.

Some possibilities arise when carbon is to be incorporated into a composition. One instance is to protect rubbers against degradation through attack by radical species leading to damage to the chemical structure of the elastomer; for this purpose rubber may incorporate a carbon filler which has been derivatised with one or more radical scavengers which could prolong the lifetime of the rubber. Similarly, in other circumstances where a polymer or elastomer composition incorporates a carbon filler, additives such as plasticisers can be grafted onto the carbon filler to prevent them from being leached from the composition. Furthermore the carbon filler can be derivatised in order to enable it to bond chemically with the polymer or elastomer and increase the mechanical strength of the composition.

A persistent problem in the use of single walled carbon nanotubes (SWCNTs) in some nanoscale electronic devices such as field effect and other transistors is the presence of so-called metallic tubes generated during their synthesis. The resulting high electrical conductivity can preclude their use in transistors. It has been found that derivatization of the carbon can suppress unwanted high conductivity and enable SWCNTs to be used in semiconductor devices. Kanungo et al. Science, vol 323, pages 234-237 (2009) derivatised metallic SWCNTs with perfluoro-2(2-fluorosulfonylethoxy) propyl vinyl ether (PSEPVE) using a [2+2] cycloaddition reaction, which resulted in a large decrease in electrical conductivity. The derivatization methods disclosed herein could be used to reduce the electrical conductivity of SWCNTs.

It will be appreciated that the example embodiments described in detail above can be modified and varied within the scope of the concepts which they exemplify. Features referred to above or shown in individual embodiments above may be used together in any combination as well as those which have been shown and described specifically. Accordingly, all such modifications are intended to be included within the scope of this disclosure as defined in the following claims.

The invention claimed is:

1. A process for derivatization of a surface of elemental carbon in solid form comprising exposing the carbon surface to an aprotic solvent containing a hydrazone molecule of the general formula

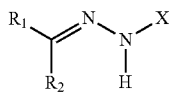

or the corresponding salt of formula

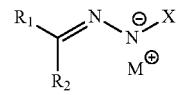

wherein $R_1$ is an organic group, $R_2$ is an organic group or hydrogen and $M^+$ is a cation and decomposing the hydrazone in the presence of elemental carbon to attach a moiety

to the elemental carbon while the group X is converted to an $X^-$ anion.

2. A process according to claim 1 wherein X is a group of the formula —$SO_2$—Y.

3. A process according to claim 2 wherein Y is an aryl sulphonyl group.

4. A process according to claim 2 wherein Y is an aromatic group bearing one or more alkyl substituents.

5. A process according to claim 1 wherein at least one of the $R_1$ and $R_2$ groups comprises an aromatic group such that the carbon atom of the >C=N—N> hydrazone group can form delocalised bonds with the aromatic ring.

6. A process according to claim 5 wherein at least one of the $R_1$ and $R_2$ groups comprises an aromatic group which is one of phenyl, napthyl or anthracenyl or comprises an aromatic ring connected to a vinyl group.

7. A process according to claim 1 wherein at least one of the $R_1$ and $R_2$ groups comprises an aromatic ring or system bearing at least one substituent which is a functional group able to undergo electrochemical redox reaction.

8. A process according to claim 7 wherein at least one of the $R_1$ and $R_2$ groups comprises an aromatic quinone or is an aromatic group bearing a nitro substituent.

9. A process according to claim 1 wherein at least one of the $R_1$ and $R_2$ groups comprises a ferrocenyl group.

10. A process according to claim 1 wherein the elemental carbon is graphite, glassy carbon, carbon fibres, carbon black, carbon paste, boron doped diamond, carbon epoxy, carbon nanotubes or graphene.

11. A process according to claim 1 wherein the elemental carbon is in particulate form and the process further comprises immobilizing the derivatized elemental carbon on an electrode.

12. A process according to claim 1 wherein the elemental carbon is an electrode.

13. A process according to claim 1 wherein decomposing the hydrozone is carried out by heating the aprotic solvent containing the hydrozone, while the solvent is in contact with the elemental carbon.

14. A process according to claim 1 wherein at least one of the $R_1$ and $R_2$ groups comprises a redox-active group able to undergo electrochemical redox reaction and the process further comprises utilizing the elemental carbon modified by the attachment of the moiety

thereto as at least part of an electrode, and connecting the electrode to means to apply voltage to the electrode and measure current flow through the electrode, thereby incorporating the modified elemental carbon into measuring apparatus.

15. A process according to claim 1 wherein at least one of the $R_1$ and $R_2$ groups comprises a redox active group able to undergo electrochemical redox reaction.

* * * * *